(12) United States Patent
Frisch et al.

(10) Patent No.: US 7,787,928 B2
(45) Date of Patent: Aug. 31, 2010

(54) METHODS, DEVICE AND SYSTEM FOR IN VIVO DETECTION

(75) Inventors: Mordechai Frisch, Moreshet (IL); Gavriel J. Iddan, Haifa (IL); Zvika Gilad, Haifa (IL); Reuven Schreiber, Haifa (IL)

(73) Assignee: Given Imaging, Ltd., Yoqneam (IL)

( * ) Notice: Subject to any disclaimer, the term of this patent is extended or adjusted under 35 U.S.C. 154(b) by 0 days.

(21) Appl. No.: 10/876,741

(22) Filed: Jun. 28, 2004

(65) Prior Publication Data

US 2005/0043617 A1  Feb. 24, 2005

Related U.S. Application Data

(63) Continuation-in-part of application No. PCT/IL03/01015, filed on Nov. 30, 2003.

(60) Provisional application No. 60/429,564, filed on Nov. 29, 2002, provisional application No. 60/482,450, filed on Jun. 26, 2003.

(51) Int. Cl.
*A61B 5/05* (2006.01)

(52) U.S. Cl. ............... 600/407; 600/109; 600/118; 600/317; 600/473; 600/476; 128/903; 348/65; 348/77

(58) Field of Classification Search ............ 600/109, 600/160, 309–310, 347, 407, 424, 427, 437, 600/476, 478, 317, 118, 473, 585; 128/903; 378/44, 62–63, 119; 348/65, 77
See application file for complete search history.

(56) References Cited

U.S. PATENT DOCUMENTS

| | | | |
|---|---|---|---|
| 3,683,389 A | 8/1972 | Hollis | |
| 3,971,362 A | 7/1976 | Pope et al. | |
| 4,038,485 A | 7/1977 | Johnston et al. | |
| 4,177,800 A | 12/1979 | Engar | |
| 4,239,040 A | 12/1980 | Hosoya et al. | |
| 4,278,077 A | 7/1981 | Mizumoto | |
| 4,439,197 A | 3/1984 | Honda et al. | |
| 4,689,621 A | 8/1987 | Kleinberg | |
| 4,741,327 A | 5/1988 | Yabe | |
| 4,744,672 A | 5/1988 | Turskey et al. | |
| 4,844,076 A | 7/1989 | Lesho et al. | |

(Continued)

FOREIGN PATENT DOCUMENTS

DE  34 40 177  5/1986

(Continued)

OTHER PUBLICATIONS

U.S. Appl. No. 10/694,092, filed Sep. 9, 2004, Iddan.

(Continued)

*Primary Examiner*—Brian Casler
*Assistant Examiner*—Baisakhi Roy
(74) *Attorney, Agent, or Firm*—Pearl Cohen Zedek Latzer LLP

(57) ABSTRACT

A system and method for in vivo diagnosis are provided. A composition including for example a radioactive marking agent and a pharmaceutically acceptable carrier is administered to a patient and an autonomous in vivo device, which may include for example an illumination source an image sensor and a radiation and/or light detector, is used to for example facilitate the difference between. normal and pathological cells in a body lumen.

21 Claims, 4 Drawing Sheets

U.S. PATENT DOCUMENTS

| | | | |
|---|---|---|---|
| 4,885,077 A | 12/1989 | Karakelie et al. | |
| 4,905,670 A | 3/1990 | Adair | |
| 4,974,929 A | 12/1990 | Curry et al. | |
| 5,001,053 A | 3/1991 | Takahashi et al. | |
| 5,026,368 A | 6/1991 | Adair | |
| 5,088,492 A | 2/1992 | Takayama et al. | |
| 5,143,054 A | 9/1992 | Adair | |
| 5,166,073 A * | 11/1992 | Lefkowitz et al. | 436/57 |
| 5,279,607 A | 1/1994 | Schentag et al. | |
| 5,385,846 A | 1/1995 | Kuhn et al. | |
| 5,395,366 A | 3/1995 | D'Andrea et al. | |
| 5,443,701 A | 8/1995 | Willner et al. | |
| 5,604,531 A * | 2/1997 | Iddan et al. | 348/76 |
| 5,762,770 A | 6/1998 | Pritchard et al. | |
| 5,814,525 A | 9/1998 | Renschler et al. | |
| 5,819,736 A | 10/1998 | Avny et al. | |
| 5,833,603 A * | 11/1998 | Kovacs et al. | 600/317 |
| 5,892,144 A | 4/1999 | Meller et al. | |
| 5,932,480 A | 8/1999 | Marsu et al. | |
| 5,970,115 A | 10/1999 | Colbeth et al. | |
| 5,993,378 A | 11/1999 | Lemelson | |
| 6,240,312 B1 * | 5/2001 | Alfano et al. | 600/476 |
| 6,471,636 B1 | 10/2002 | Sano et al. | |
| 6,632,175 B1 * | 10/2003 | Marshall | 600/309 |
| 6,918,872 B2 * | 7/2005 | Yokoi et al. | 600/129 |
| 6,951,536 B2 * | 10/2005 | Yokoi et al. | 600/128 |
| 7,011,814 B2 * | 3/2006 | Suddarth et al. | 424/9.2 |
| 7,241,262 B2 * | 7/2007 | Adler et al. | 600/130 |
| 2001/0017649 A1 | 8/2001 | Yaron | |
| 2001/0031502 A1 | 10/2001 | Watson, Jr. et al. | |
| 2001/0035902 A1 | 11/2001 | Iddan et al. | |
| 2001/0051766 A1 * | 12/2001 | Gazdzinski | 600/309 |
| 2001/0053535 A1 | 12/2001 | Bashir et al. | |
| 2002/0042562 A1 | 4/2002 | Meron et al. | |
| 2002/0103417 A1 * | 8/2002 | Gazdzinski | 600/109 |
| 2002/0111544 A1 | 8/2002 | Iddan | |
| 2002/0198439 A1 | 12/2002 | Mizuno | |
| 2003/0139661 A1 * | 7/2003 | Kimchy et al. | 600/407 |
| 2003/0171648 A1 | 9/2003 | Yokoi et al. | |
| 2003/0171649 A1 | 9/2003 | Yokoi et al. | |
| 2003/0171652 A1 | 9/2003 | Yokoi et al. | |
| 2003/0187349 A1 | 10/2003 | Kaneko et al. | |
| 2004/0027459 A1 | 2/2004 | Segawa et al. | |
| 2004/0054278 A1 * | 3/2004 | Kimchy et al. | 600/407 |
| 2005/0004474 A1 * | 1/2005 | Iddan | 600/476 |
| 2005/0065441 A1 * | 3/2005 | Glukhovsky | 600/476 |
| 2005/0148842 A1 * | 7/2005 | Wang et al. | 600/407 |

FOREIGN PATENT DOCUMENTS

| | | |
|---|---|---|
| JP | 57-45833 | 3/1982 |
| JP | 01-107737 A | 4/1989 |
| JP | 3289779 | 12/1991 |
| JP | 4109927 | 4/1992 |
| JP | 4180736 | 6/1992 |
| JP | 5015515 | 1/1993 |
| JP | 05-200015 A | 8/1993 |
| JP | 7289504 | 11/1995 |
| JP | 2001 137182 | 5/2001 |
| JP | 2001 224551 | 8/2001 |
| JP | 2001 224553 | 8/2001 |
| WO | WO 92/21307 | 12/1992 |
| WO | WO 97/33513 | 9/1997 |
| WO | WO 98/11816 | 3/1998 |
| WO | WO 01/07919 | 2/2001 |
| WO | WO 01/08548 | 2/2001 |
| WO | WO 01/50941 | 7/2001 |
| WO | WO 01/65995 | 9/2001 |
| WO | WO 02/26103 | 4/2002 |
| WO | WO 02/058531 | 8/2002 |
| WO | WO 02/067593 | 8/2002 |
| WO | WO 03/094723 | 11/2003 |
| WO | WO 2004/014227 | 2/2004 |
| WO | WO 2004/049947 | 6/2004 |

OTHER PUBLICATIONS

International Search Report International Application No. PCT/IL04/00569 International Filing Date : Jun. 27, 2004.

* cited by examiner

METHODS, DEVICE AND SYSTEM FOR IN VIVO DETECTION

RELATED APPLICATION DATA

This application claims benefit from U.S. provisional application Ser. No. 60/482,450, filed on Jun. 26, 2003, entitled METHODS, DEVICE AND SYSTEM FOR IN VIVO DETECTION which is incorporated in its entirety by reference herein. This application is also a continuation in part of PCT Patent Application PCT/IL03/01015 filed 30 Nov., 2003 entitled METHOD, DEVICE AND SYSTEM FOR IN VIVO DIAGNOSIS which is incorporated in its entirety by reference herein, which in turn claims priority from U.S. provisional application Ser. No. 60/429,564, filed on Nov. 29, 2002, which is incorporated in its entirety by reference herein.

FIELD OF THE INVENTION

The present invention relates to in vivo diagnosis. More specifically, the invention relates to methods, device and system for detection of pathologies or other medical conditions in body lumens, for example, in the gastrointestinal (GI) tract.

BACKGROUND OF THE INVENTION

Pathologies of the GI tract (which may include the pharynx, esophagus, stomach, duodenum, small bowel, and colon) include, among others, esophageal carcinoma, peptic ulcer diseases, colorectal carcinoma and inflammatory bowel diseases (e.g., ulcerative colitis and Crohn's disease). Early pancreatic cancer may manifest itself through neoplasms released into the small intestine by the pancreas. Gastric cancer is a major cause of death worldwide especially in Far East countries. The major type of gastric cancer is adenocarcinoma, which can be further categorized into an intestinal type and a diffuse type. Intestinal type lesions are frequently ulcerative and occur in the distal stomach more often than the diffuse type. These lesions are associated with a worse prognosis than the intestinal type. Colon and rectal cancers accounts for approximately 20% of all deaths due to malignant disease in the United States. Also, cancer of the pancreas is considered the fifth leading cause of cancer deaths in the United States. Other GI tract pathologies may include bleeding and disorders such as protein loosing enteropathy (PLE).

Delayed detection of GI tract cancers and other pathologies is a major factor contributing to an overall poor prognosis. Signs of early stages of GI tract cancers may be vague and nonspecific. The deep anatomical location of organs and parts of the GI tract may also add to the low yield of early detection. Often, gastrointestinal neoplasms arise in premalignant lesions which are only partially accessible or visible by regular endoscopy, laparoscopy or radiology.

Among known modalities used to distinguish normal from malignant tissue, are optically based techniques such as photodynamic diagnosis (PPD), also known as fluorescence diagnosis, and vital staining techniques, such as chromoendoscopy. Other techniques include the use of labeled tumor targeted molecules such as, labeled tumor specific antibodies. These techniques are based on specific accumulation of administered agents, such as monoclonal antibodies, photosensitizers (in PPD) or pigments (in chromoendoscopy) and detection of the accumulated agents.

These techniques are used in various medical fields. Radioactively labeled antibodies, typically intravenously administered to a patient, can be detected from outside the patient's body by a gamma camera, which can be universally found in all nuclear medicine departments. The image captured by the camera identifies the existence, location and extent of the radiolabeled pharmaceutical thus identifying the sites of tumor. Other detection methods utilize devices such as catheters, laparoscopes and endoscopes for the detection of the specifically accumulated agents. Integral illumination and imaging capabilities of these devices may be used for detecting photosensitizers and/or other pigments. Also, invasive devices or devices such as endoscopes (e.g., colonoscopes) may be equipped with a radiation detector for detecting radioactively labeled antibodies. For example, a colonoscope may have a scintillation crystal mounted on the tip of an optical fiber wave guide. The optical fiber is housed within a shielded tube which is inserted into the colonoscope and extends to within 4 mm of the open end of the colonoscope, the remaining length of the tubing serving as a collimator.

The use of gamma cameras from outside of the body may require a patient to be exposed to large amounts of typically high penetrating radioactive labeling. In vivo detection methods such as endoscopic (e.g., colonoscopic) examinations, usually require patient preparation and are typically stressful for patients, leading to low patient compliance and to low yield of early detection. Additionally, a large part of the GI tract (for example, most of the small intestine) is inaccessible to endoscopes. Thus, endoscopic examinations provide only a partial answer to the needs of early detection and they are not perceived as beneficial in wide scale screening for cancers.

There is thus a need for a patient friendly detection tool and method, capable of safely screening even the difficult to reach parts of body lumens, for early signs of diseases such as cancer.

SUMMARY OF THE INVENTION

Methods, devices and systems according to embodiments of the invention are used, inter alia, to facilitate the difference between normal and pathological (e.g., malignant or other types) cells in a body lumen. Embodiments of the invention relate to a typically non-invasive autonomous ingestible device, which enables in situ visualization and/or detection of, for example, neoplastic or malignant cells or tissue, or other pathological tissue even in areas that are inaccessible to endoscopes.

According to embodiments of the invention a system is provided for diagnosing malignancy or other pathologies in the GI tract. The system, according to one embodiment, includes a composition including at least a radioactively labeled marking agent and a pharmaceutically acceptable carrier. Also included in the system, according to an embodiment of the invention, is an ingestible device capable of detecting ionizing radiation in vivo.

According to embodiments of the invention a radioactively labeled marking agent may include molecules or compounds that selectively and/or differentially adhere to tumors in endo luminal tissues. According to another embodiment a radioactively labeled marking agent may include targeting agents, such as tumor specific antibodies.

In one embodiment, there is provided an ingestible autonomous in vivo device capable of detecting ionizing radiation in vivo. According to some embodiments the in vivo device includes a scintillation crystal. According to another embodiment of the invention the in vivo device may also include an image sensor and/or a transmitter, typically a wireless transmitter, for transmitting data to a receiving unit that is located externally to the patient.

A method for detection of neoplasms and/or malignancies in vivo, according to an embodiment of the invention, includes the step of administering to a person a radioactively labeled marking agent and the step of detecting ionizing radiation. According to one embodiment this is performed by inserting into a body lumen an autonomous, typically wireless device capable of detecting ionizing radiation. An autonomous device, according to embodiments of the invention may be swallowed. According to other embodiment an autonomous device may be capable of scanning, in close proximity, a body lumen wall (e.g., a GI tract wall). Thus, easy detection of low energy and/or low penetrating labeling is possible and a typically low hazardous detection device and method are provided according to embodiments of the invention.

DETAILED DESCRIPTION OF THE INVENTION

In the following description, various aspects of the invention will be described. For purposes of explanation, specific configurations and details are set forth in order to provide a thorough understanding of the invention. However, it will also be apparent to one skilled in the art that the invention may be practiced without the specific details presented herein. Furthermore, well-known features may be omitted or simplified in order not to obscure the invention.

Figure 1:
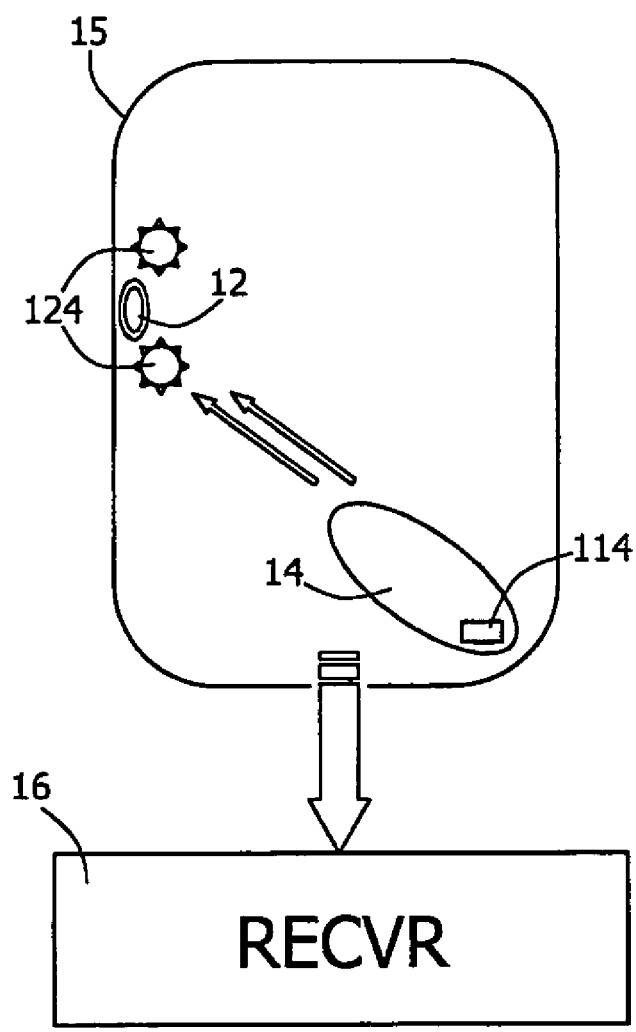
FIG. 1 is a block diagram schematically illustrating a system according to an embodiment of the invention.

According to some embodiments the invention is based on specifically marking neoplastic, for example, malignant, cells or tissue. Other cells or conditions may also be marked according to embodiments of the invention. A system for in vivo diagnosis, according to an embodiment of the invention is schematically illustrated in FIG. 1. The system includes a labeled marking agent 12, an in vivo detecting device 14 and a receiving unit 16. The labeled marking agent 12 may typically be contained in a composition, which includes at least a pharmaceutically acceptable carrier 124. According to an embodiment of the invention the composition may be introduced into a patient's body 15, for example, intravenously, in which the labeled marking agent 12 may show different patterns for different in vivo conditions, such as pathological and non pathological conditions. According to one embodiment labeled marking agent 12 typically migrates and adheres to dysplasias, tumors or malignant or cancerous cells. The term dysplasias may be understood to include, inter alia, neoplasms, lesions and/or malignancies. According to other embodiments the marking agent 12 may typically migrate to and/or adhere to a normal tissue while specifically not to pathological cells or tissue. According to other embodiments distribution patterns and/or dynamics of labeled marking agent 12 may indicate an in vivo condition. In alternate embodiments marking agent 12 may migrate to and/or adhere to other cells, structures or substances, such as pathological cells or structures or substances associated with pathology; further, marking agent 12 may migrate to and/or adhere to other cells, structures or substances, which may not be associated with a pathology.

According to an embodiment of the invention the detecting device 14 is introduced into a patient's body lumen (such as the GI tract, although other lumens may be so examined) and detects marked areas. According to some embodiments the detecting device 14 may include an image sensor, and images of the body lumen environment may be obtained together with detecting marked areas. The obtained data (including image data) is transmitted to a typically external receiving unit 16 for further analysis and diagnosis. Receiving unit 16 may include image processing capabilities. According to some embodiments image processing takes place either prior to or after the image data is transmitted to the receiving unit.

According to embodiments of the invention the labeled marking agent 12 typically includes a radionuclide. According to one embodiment the radionuclide may be high linear energy transfer (LET) such as beta, alpha, Auger or low energy conversion electron emitters; other marking agents or radionuclides may be used. According to one embodiment, labeled marking agent 12 includes tumor marker targeted molecules. Tumor markers may be molecules occurring in blood or tissue that are associated with cancer. Typically, tumor markers are cancerous cells or products of cancerous cells and they represent aberrant production of what may be a typically normal element. Some markers, such as antibodies, are produced in response to the presence of cancer. Tumor marker targeted molecules typically have a high affinity to tumor markers and, under certain conditions, adhere to tumor markers in a liquid environment. These may include antigens having specificity to tumor marker antibodies. Alternatively, tumor marker targeted molecules may include antibodies specific to tumor marker antigens. According to an embodiment of the invention a tumor marker targeted molecule may be modified to include a radionuclide moiety.

According to another embodiment labeled marking agent 12 includes molecules or compounds that migrate to or adhere to normal tissue and/or cells, for example, carbomer compounds, protein compounds (such as serum albumin) or glucose analogs (e.g., 2-fluoro-2-deoxy-D-glucose) which are not metabolized and are thus accumulated in glucose uptaking cells. Marking agent 12 may include molecules or compounds that migrate to or adhere to other types of cells, structures or substances.

According to an embodiment of the invention the in vivo detecting device 14 may be for example an ingestible capsule, which may include a radiation detector unit 114. Configurations other than a capsule may be used; for example an endoscope may be used. The device may also include an illumination source for illuminating a body lumen (e.g., the GI tract), an image sensor for obtaining images of the body lumen and a transmitter (e.g., 26 in FIG. 2A) for transmitting image or other data to the receiving unit 16. Receiving unit 16 is typically located outside a patient's body and may include an antenna or antenna array, for receiving image and possibly other data from the device 14, a receiver storage unit, for storing image and other data, a data processor, a data processor storage unit, and an image monitor, for displaying, inter alia, the images transmitted by the transmitter and recorded by the receiving unit 16. Typically, the receiver and receiver storage unit are small and portable, and may be worn on the patient's body during recording of the images. Typically, data processor, data processor storage unit and monitor are part of a personal computer or workstation, which may include standard components such as a processor, a memory, a disk drive, and input-output devices, although alternate configurations are possible. In alternate embodiments, the data reception and storage components may be of another configuration. Processing capabilities, for example for processing real image data, may be included in the receiving unit or in the workstation.

In one embodiment, all of the components may be sealed within the device body (the body or shell may include more than one piece); for example, an imager, illumination units, power units, and transmitting and control units, may all be sealed within the device body. Aspects of the various embodiments disclosed herein are combinable with the other embodiments disclosed herein.

Figure 2A:
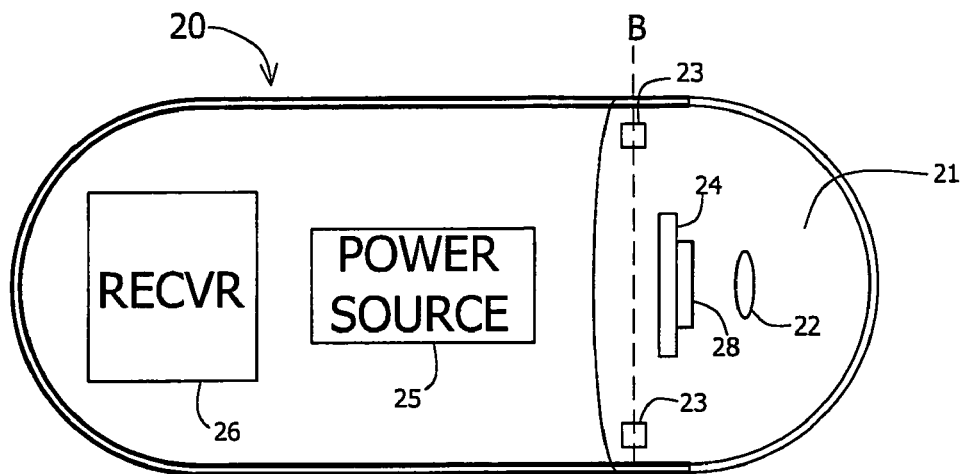
FIGS. 2A-2D show schematic illustrations of in vivo detecting devices according to embodiments of the invention.

Reference is now made to FIGS. 2A-D, which schematically illustrate in vivo detecting devices, such as device 14 of FIG. 1, according to embodiments of the invention. Referring to FIG. 2A, in an exemplary embodiment, the device 20 is an autonomous capsule shaped device capable of detecting radiation from within a body lumen. The device may be of a shape other than a capsule, and need not be swallowable. Typically, device 20 includes at least one radiation detector unit 28 and a transmitter 26. Typically, radiation detecting unit 28 includes a scintillation detector, which measures radiation by detecting tiny flashes of light which radiation produces in certain materials. Other suitable radiation detection units may be used These light flashes (e.g., scintillation) are converted to electrical pulses and, when fed into suitable electronics, can discriminate between different types of radiation and even between different energies of the same radiation. The detector systems (such as detector unit 28) may include two components which are optically coupled. The first is a scintillator which may be a solid (e.g., crystal, powder etc.), gas or liquid which emits light pulses when radiation deposits energy in it. The second component is a photomultiplier which converts this light pulse into a pulse of electric current. NaI (T1), CsI (T1) and CsI (Na) are examples of scintillation crystals for use in detectors of ionizing radiation such as gamma-rays, x-rays, alpha and beta particles. Also, for example, Ce-141 is sometimes used for gastrointestinal tract diagnosis and measuring regional myocardial blood flow. Positron emission detectors may also be used. Other components or sets of components may be used.

Figure 2B:
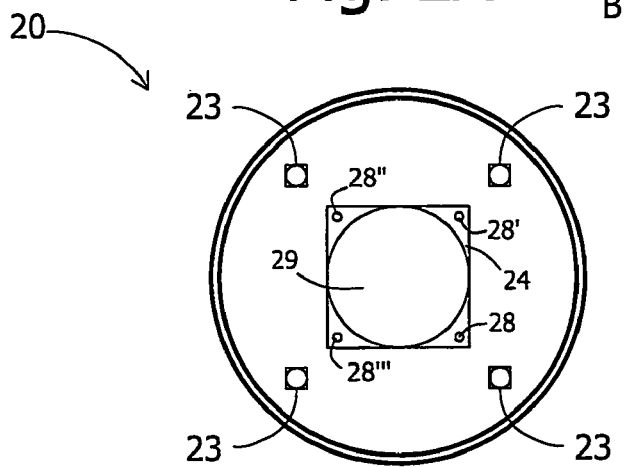
Figure 2C:
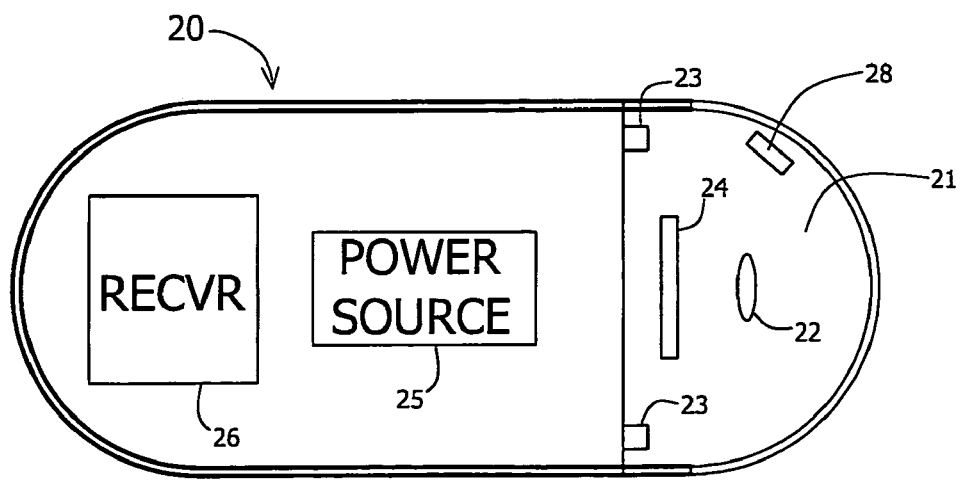
Figure 2D:
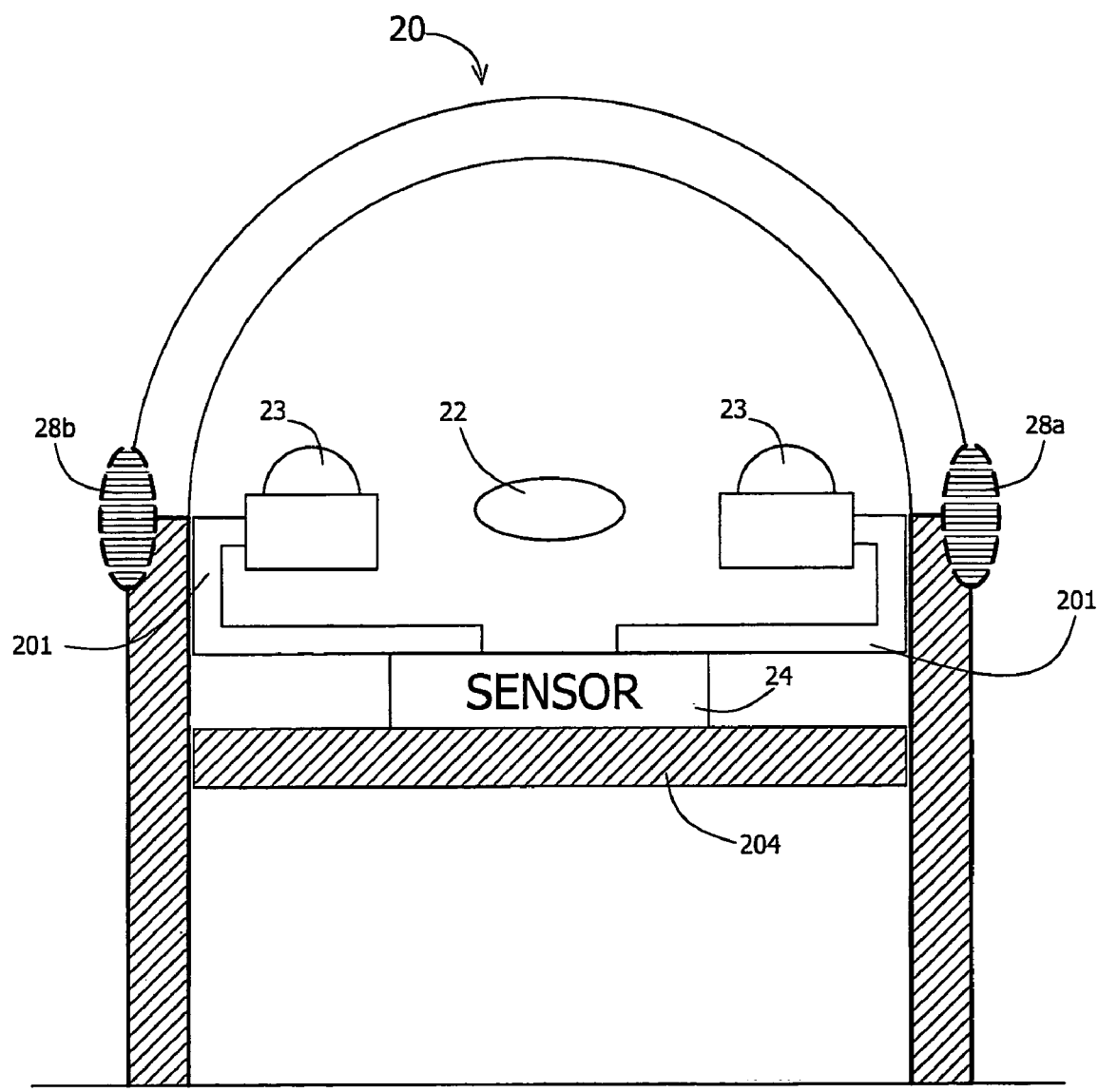

According to some embodiments the device 20 may include additional sensors or elements such as a light sensor 24 and at least one illumination source 23 (two illumination sources 23 and four illumination sources 23 are included in FIGS. 2A and 2B accordingly, for illustrative purposes; other numbers may be used). The light sensor 24 may be any suitable scintillation array, such as a silicon array. According to some embodiments the light sensor 24 may include thin sheets of scintillating material, such as, a plastic scintillator or zinc sulphide embedded in a transparent tape.

According to some embodiments the light sensor 24 may be an image sensor such as a CMOS, CCD or any other suitable in vivo image sensor. According to some embodiments the device 20 may include an optical dome 21, which provides a generally transparent cover for the detecting elements (such as the detector unit 28, the light source 23, the light sensor 24 and any accompanying electronic circuits), provides a sealed barrier to bodily fluids, and may perform other functions (such as holding optical elements). An optical system 22, including, for example, one or more optical elements, such as one or more lenses or composite lens assemblies, or any other suitable optical elements, may aid in focusing reflected light onto the light sensor 24 and performing other light processing, typically for obtaining images. Radiation detector unit 28 may cover all (e.g., FIG. 2A) or some (e.g., FIG. 2B) of the cells (e.g., pixels) of the light sensor 24.

Device. 20 typically includes a transmitter 26, for transmitting image and possibly other (e.g., non-image) information to a receiving device, and may include other components, such as, for example, a compression module for compressing data According to one embodiment the transmitter 26 is an ultra low power radio frequency (RF) transmitter with high bandwidth input, possibly provided in chip scale packaging. The transmitter 26 may transmit wirelessly via an antenna The transmitter 26 may also include circuitry and functionality for controlling the device 20. For example, a master clock included in transmitter 26 may control illumination functions of the device. Typically, the device includes a power source 25, such as one or more batteries. For example, the power source 25 may include silver oxide batteries, lithium batteries, or other electrochemical cells having a high energy density, or the like. Other power sources may be used. Other components and sets of components may be used. For example, the power source may be an external power source transmitting power to the device, and a controller separate from the transmitter 26 may be used.

According to one embodiment (for example, as described in FIG. 2A) a detector unit 28 is placed upon an image sensor 24 (in one embodiment a CMOS imager, but other types of imagers, such as CCD imagers, may be used), covering substantially most or all of the pixels of light sensor 24. According to some embodiments the light sensor 24 is a CMOS image sensor chip of approximately 4.5 mm×4.5 mm in which the light sensitive area may be about 2.5 mm×2.5 mm. In alternative embodiments other image sensors may be used and/or other shapes and sizes may be utilized. According to one embodiment a radiation detector unit 28 includes an approximately 1.5 mm×1.5 mm or a 2.5 mm×2.5 mm scintillation crystal. According to some embodiments the radiation detector unit 28 includes collimating means. Other types of detector units may be used.

According to another embodiment (for example, as described in FIG. 2B, which is a cross section taken along line B-B in FIG. 2A) detectors 28, 28', 28" and 28''' (which may be the same or different detectors) are placed over small portions of the light sensor 24 leaving other portions (e.g., portion 29) free for obtaining images of the body lumen.

According to yet another embodiment (for example, as described in FIG. 2C) a detector 28 is placed within the optical dome 21, or in another position, not in close proximity to the light sensor 24, but within view of the light sensor 24. According to some embodiments scintillation from detector unit 28 will be optically registered on light sensor 24.

According to yet other embodiments (for example, as described in FIG. 2D) more than one radiation detector unit is used. According to one embodiment radiation detector units 28a and 28b may be located on device 20 such that they are not in direct view of light sensor 24. Diverters, such as light diverter 201, may be used to channel light produced in detector units 28a and/or 28b to light sensor 24. Scintillation light may be directed to any suitable portion of light sensor 24, such as, for example, to a corner of the light sensor 24. Any suitable diverters may be used, such as optical fibers or tubes, light pipes, prisms, mirrors, etc. According to some embodiments a light sensor 24 may be part of the radiation detecting system in which a processor 204 may be utilized for on board processing of radiation data. For example, processor 204 may be used in combination with tomographic techniques to provide PET (positron emission tomography) like information According to one embodiment short half life (in the order of minutes) radioisotopes may be used which emit a positron in the process of decay. When this positron collides with an electron, the two particles annihilate each other, and produce two photons traveling in opposite directions. Two detectors positioned opposite one another, for example as detector units

28a and 28b, can be used to detect the event. When two photons are detected within some small time window, it is assumed that they came from one annihilation, and this annihilation was on the line connecting the detection points. Suitable processing may occur within processor 204. Processing may also be done externally to the patient's body, for example in external receiving unit 16 or in a personal computer or workstation as described above.

In accordance with embodiments of the invention, including the embodiments described above, compositions including a labeled agent are administered to a patient and after a metabolic period (e.g., 1-24 hours; other periods may be used), a detecting device, such as device 20, is introduced in vivo for monitoring a body lumen. According to one embodiment, radiolabled tumor marker targeted molecules or other agents according to embodiments of the invention, are adhered to pathological sites, such as carcinomas and/or other cancerous cells within a body lumen or within a body lumen wall. According to other embodiments labeled compounds are distributed in vivo in a typical pattern, which may be indicative of an in vivo condition. Device 20, which is typically an autonomous detecting device, may scan the body lumen environment and walls. Radiation energy emitted from a radiolabled marker, for example at a pathological site within the body lumen, will be deposited in the detection unit 28 (e.g., in a scintillation crystal) and the resultant light pulses will be detected by a light sensor (e.g., light sensor 24). Typically, a signal is generated and transmitted to an external receiving unit, thereby alerting an external operator. According to some embodiments (for example as described in FIGS. 2A and 2B) scintillation may be directly detected on light sensor 24 and processed by circuitry of light sensor 24. According to other embodiments, for example as described in FIGS. 2C and 2D, a detecting system may include dedicated circuitry for processing scintillation occurring within the detector unit 28 and for presenting a signal that may be directly transmitted (e.g., by transmitter 26 or another transmitter) to an external receiving unit or that may be visible to light sensor 24 and thus transmitted together with image data that is transmitted from light sensor 24.

According to some embodiments, the location of the device 20 may be known, for example, by methods known in the art, such that the location of pathology (as indicated by a site of radiation) may also be known. According to other embodiments device 20 may be immobilized in vivo to provide monitoring of a specific region or area within a body lumen. Some methods of immobilizing an in vivo device are described, for example, in International Application WO 02/26103 and published US application US-2002-0042562-A1, each of which is assigned to the common assignee of the present invention, and each of which is incorporated by reference herein in its entirety.

According to one embodiment radiolabled tumor marker targeted molecules are utilized to specifically mark neoplastic and/or malignant cells. Compositions according to embodiments of the invention are administered to a patient and after a metabolic period (e.g., 24 hours; other periods may be used), a detecting device, such as device 20, is introduced in vivo for scanning and/or monitoring a body lumen. According to embodiments of the invention even typically difficult to reach parts of the GI tract, such as the small intestine, can be scanned/monitored. Device 20 may scan a body lumen by passing through the lumen. Typically, a device according to embodiments of the invention may pass through body lumens in proximity to the lumen walls. Monitoring a body lumen may be performed by scanning the lumen wall to identify radiation (for example, a radiation above a predetermined background level). According to one embodiment scanning may typically include having the device 20 come into proximity or even contact with an endo-luminal area to be scanned. For example, a capsule shape device may be propelled through a person's small intestine due to the natural peristaltic movements of the intestine, thus, enabling the device to come into proximity with essentially the whole small intestine and to scan the small intestine. According to some embodiments high sensitivity detection of alpha particles or other typically short range emitting markers can be obtained since the device 20 can come in close proximity to the marker molecule itself. According to some embodiments detection of radiation within a colon may be done without putting the patient through a typically unpleasant prep.

According to some embodiments the device 20 and a suitable reception system or receiving unit may be adapted from, and may contain structures and may be functionally similar to, embodiments described in U.S. Pat. No. 5,604,531 to Iddan et al., and/or in published International Application WO01/65995 to Glukhovsky et al, each of which is incorporated by reference in its entirety. For example, a transmitting and reception, and a display system, may be similar to or adapted from such embodiments. According to these embodiments detection of radiation may be accompanied by obtaining images of the scanned lumen walls.

Figure 3:
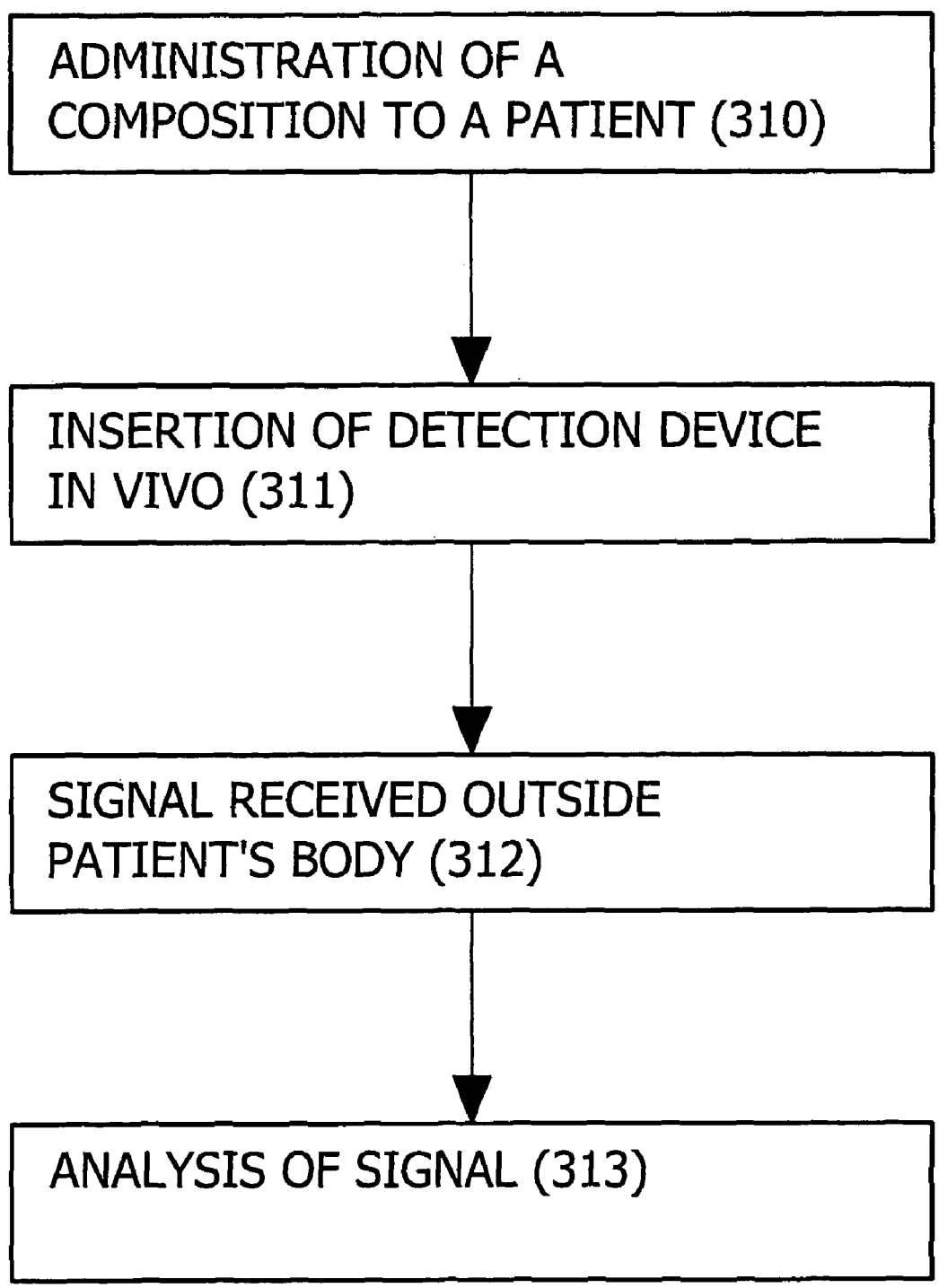
FIG. 3 is a flowchart depicting a method of detecting malignant and/or cancerous cells or tissue, according to an embodiment of the invention.

A method for detecting malignant and/or cancerous cells or tissue, according to an embodiment of the invention is depicted in FIG. 3.

According to one embodiment a radio labeled tumor marker targeted complex is administered to a patient (310). A detecting device according to embodiments of the invention is then inserted in vivo (311) and a signal indicating radiation is received out side of the patient's body (312). According to some embodiments the received signal may be analyzed and/or compared to a pre determined radiation level (e.g., a background level) and a decision may be made regarding the significance of the detected radiation (313). For example, if a detected radiation is above a predetermined radiation level pathology or other condition may be indicated whereas if a detected radiation is below a predetermined radiation level it may be determined that no pathology or condition has been detected. Alternatively, a certain distribution of radiation may be determined to indicate a normal condition whereas another distribution may indicate pathology such as bleeding or other gastroenteropathies.

According to some embodiments tumor marker targeted molecules may include antibodies to antigenic determinants associated with cancer, such as, CA19.9 (an antigenic determinant associated with cancers such as pancreas, colorectal and gastric) and CEA (an antigenic determinant associated with cancers such as pancreas, colorectal, liver and gastric). According to other embodiments tumor marker targeted molecules may include antigenic determinants having affinity to antibodies associated with cancer, such as Gastric Mucin, which is specific to an IgG antibody associated with stomach and colon cancers. Many tumor marker targeted molecules are commercially available, for example, 116-NS-19-9 is a CA19.9 specific antibody and mCEA is a CEA specific antibody, both available from ARUP Laboratories of the Fitzgerald Industries. These molecules may be modified as is known in the art to include a radionuclide moiety. For example, CEA monoclonal antibodies labeled with I-125 have been described. According. to some embodiments, through formation of an antibody-antigen complex, a tumor marker targeted molecule is linked to a target cancer cell and will adhere to that cell even after washing of the tissue.

According to some embodiments a composition may include radiolabeled serum albumin or glucose analogs.

In methods according to embodiments of the invention, a composition may be administered orally, parenterally, by inhalation spray, topically, rectally, nasally, buccally, vaginally or via an implanted reservoir in dosage formulations containing conventional non-toxic pharmaceutically-acceptable carriers, adjuvants and vehicles. The term parenteral as used herein may include, inter alia, subcutaneous, intravenous, intramuscular, intraperitoneal, intrathecal, intraventricular, intrasternal or intracranial injection and infusion techniques. The compounds may also be administered in the form of sterile injectable preparations, for example, as sterile injectable aqueous or oleaginous suspensions. These suspensions can be formulated according to techniques known in the art using suitable dispersing or wetting agents and suspending agents. The sterile injectable preparations may also be sterile injectable solutions or suspensions in non-toxic parenterally-acceptable diluents or solvents, for example, as solutions in 1,3-butanediol. Among the acceptable vehicles and solvents that may be employed are water, Ringer's solution and isotonic sodium chloride solution. In addition, sterile fixed oils are conventionally employed as solvents or suspending mediums. For this purpose, any bland fixed oil such as a synthetic mono- or di-glyceride may be employed. Fatty acids such as oleic acid and its glyceride derivatives, including olive oil and castor oil, especially in their polyoxyethylated forms, are useful in the preparation of injectables. These oil solutions or suspensions may also contain long-chain alcohol diluents or dispersants. Additionally, the compounds may be administered orally in the form of capsules, tablets, aqueous suspensions or solutions. Tablets may contain carriers such as lactose and corn starch, and/or lubricating agents such as magnesium stearate. Capsules may contain diluents including lactose and dried cornstarch. Aqueous suspensions may contain emulsifying and suspending agents combined with the active ingredient. The oral dosage forms may further contain sweetening and/or flavoring and/or coloring agents. The compounds may further be administered rectally in the form of suppositories. These compositions can be prepared by mixing the drug with suitable non-irritating excipients which are solid at room temperature, but liquid at rectal temperature such that they will melt in the rectum to release the drug. According to some embodiments such excipients include cocoa butter, beeswax and polyethylene glycols.

The compounds may also be administered topically. The compounds can be formulated into suitable ointments, lotions or creams containing the compounds suspended or dissolved in, for example, mixtures with one or more suitable materials such as, mineral oil, limpid petrolatum, white petrolatum, propylene glycol, polyoxyethylene polyoxypropylene compound, emulsifying wax, sorbitan monostearate, polysorbate 50, cetyl ester wax, cetearyl alcohol, 2-octyldodecanol, benzyl alcohol and water. Topical application to the lower intestinal tract can be effected in rectal suppository formulations (see above) or in suitable enema formulations. Compositions and methods according to embodiments of the invention also may utilize controlled release technology, as known in the art. In cases where there is more than one composition, each of the compositions can be manufactured in a different form. In another embodiment, the compositions can be manufactured in the same form. In alternate embodiments compositions according to embodiments of the invention may be sprayed onto a lumen wall by methods known in the art, for example, by use of an endoscope or by use of burst release capsules. Tablets that release active ingredients upon changes in environmental pH or temperature are known and may be utilized according to certain embodiments of the invention. Other additives may be included in compositions according to embodiments of the invention. Appropriate additives may be selected such that they do not interfere with the activity of the targeted molecule and such that they may facilitate the reaction of the targeted molecule with a tumor marker. In some instances, an additive is selected to increase the specificity, toxicity, solubility, serum stability, and/or intracellular availability of the targeted moiety.

Pharmaceutically compatible binding agents and adjuvant materials can be included as part of the composition.

The step of administering a labeled agent to a patient may be preceded or followed by preparation steps, which may include washing the lumen wall, for example by ingesting a volume of water. Other preparation steps may include having the patient fast prior to administration or emptying of lumens, such as the large intestine. However, one advantage of detecting methods according to embodiments of the invention includes the fact that labeling may be detected in all portions of the GI tract (including, for example, the large intestine) with out having to prepare the patient at all.

Inserting an in vivo device into body lumens may be accompanied by positioning of the patient so as to ensure proper positioning of the device in the lumen and full scanning of the lumen. It will be appreciated that the positioning and rotating of the patient may enhance positioning and scanning by the device of the lumen being inspected. For example, swallowing a device while being horizontally positioned ensures the device stays in the esophagus for a desired amount of time. However, it will be appreciated that liquids and/or the device 20 reach the stomach in a matter of minutes, the small intestine in the range of 1-3 hours and the large intestine in about 6 hours. Thus, the timing of the different steps may be adjusted as needed.

According to some embodiments of the invention there are provided kits for diagnosing enteropathies and/or malignant or cancerous cells or tissues. According to one embodiment a kit may contain at least one composition which includes at least a radio labeled agent. According to another embodiment a kit may also contain a typically single use wireless in vivo detecting device.

The kits, devices, methods and systems according to embodiments of the invention enable easy and patient friendly in situ detection of, for example, neoplastic or malignant cells or tissue in areas that are typically inaccessible to endoscopes.

It will be appreciated by persons skilled in the art that the present invention is not limited to what has been particularly shown and described hereinabove. Rather the scope of the present invention is defined only by the claims, which follow:

What is claimed is:
1. An autonomous in vivo device comprising:
an optical dome;
an illumination source for illuminating a body lumen through the optical dome;
a radiation detector unit capable of generating light pulses within said device;
a image sensor for imaging the body lumen as a result of illumination reflected from said body lumen and received through the optical dome, and comprising at least first and second non-overlapping portions, each portion having one or more pixels; and
a transmitter,
wherein said radiation detector unit is placed directly on said first portion of pixels of the image sensor such that said first portion does not receive illumination reflected from said body lumen, and wherein said second portion of pixels of the image sensor is configured for capturing images of a body lumen.

2. The device according to claim 1 wherein said radiation detector unit comprises a scintillator.

3. The device according to claim 2 wherein said scintillator is selected from the group consisting of solid, gas, liquid.

4. The device according to claim 2 wherein said scintillator is selected from the group consisting of: NaI(T1), CsI(T1), CsI(Na), Ce-141.

5. The device according to claim 1 wherein said radiation detector unit comprises a photomultiplier.

6. The device according to claim 1 wherein said radiation detector unit is configured to detect ionizing radiation, said ionizing radiation selected from the group consisting of: gamma-rays, x-rays, alpha particles and beta particles.

7. The device according to claim 1, wherein said device is autonomous.

8. The device according to claim 1, wherein said image sensor is selected from the group consisting of a CMOS and a CCD.

9. The device according to claim 1, wherein said transmitter is a radio frequency transmitter.

10. The device according to claim 1, wherein said radiation detector unit is placed within an optical dome.

11. The device according to claim 1, comprising a processor.

12. The device according to claim 11, wherein said processor is a radiation data processor.

13. The device according to claim 1, comprising a power source.

14. The device according to claim 13, wherein said power source is an external power source.

15. An autonomous in vivo device comprising:
an optical dome;
a radiation detector unit capable of generating light pulses within said device;
an illumination source for illuminating a body lumen through the optical dome;
an image sensor for imaging the body lumen as a result of illumination reflected from said body lumen and received through the optical dome, and comprising at least first and second non-overlapping portions, each portion having one or more pixels;
an optical system for focusing light from said illumination source reflected from said body lumen through said optical dome onto said first portion of the image sensor for obtaining images of the body lumen;
a light diverter for diverting the direction of the light pulses from said radiation detector towards said second portion of the image sensor; and
a transmitter.

16. The device according to claim 15 wherein said radiation detector unit comprises a scintillator.

17. The device according to claim 16 wherein said scintillator is selected from the group consisting of: solid, gas, liquid.

18. The device according to claim 15 wherein said scintillator is selected from the group consisting of: NaI(T1), CsI (T1), CsI(Na), Ce-141.

19. The device according to claim 15 wherein said radiation detector unit comprises a photomultiplier.

20. The device according to claim 15 wherein said radiation detector unit is configured to detect ionizing radiation, said ionizing radiation selected from the group consisting of gamma-rays, x-rays, alpha particles and beta particles.

21. The device according to claim 15, wherein said light diverter is selected from the group consisting of optical fibers, light pipes, prisms, and mirrors.

* * * * *